United States Patent
Lee et al.

(10) Patent No.: US 8,124,756 B2
(45) Date of Patent: Feb. 28, 2012

(54) METHOD OF PREPARING 5'-AMINO-LINKER OLIGONUCLEOTIDES DERIVATIVES AND ANALOGOUS 5'-LABELED-LINKER OLIGONUCLEOTIDES THEREFROM

(75) Inventors: Jung-Hwan Lee, Pohang-si (KR); Hyun-Gu Kang, Daegu (KR); Sung-Ho Ryu, Pohang-si (KR); Jong-In Kim, Pohang-si (KR); Sun-Hak Lee, Daejeon (KR); Hye-Jung Lee, Daegu (KR); Eun-Jung Jang, Pohang-si (KR)

(73) Assignees: Postech Academy-Industry Foundation, Nam-Ku, Kyungsangbuk-Do, Pohang (KR); Posco, Nam-Ku, Kyungsangbuk-Do, Pohang-Shi (KR)

( * ) Notice: Subject to any disclaimer, the term of this patent is extended or adjusted under 35 U.S.C. 154(b) by 42 days.

(21) Appl. No.: 12/559,666

(22) Filed: Sep. 15, 2009

(65) Prior Publication Data
US 2010/0093994 A1    Apr. 15, 2010

Related U.S. Application Data

(60) Provisional application No. 61/097,365, filed on Sep. 16, 2008.

(51) Int. Cl.
*C07H 21/00*    (2006.01)

(52) U.S. Cl. .................................. 536/25.32; 536/25.34
(58) Field of Classification Search .................. None
See application file for complete search history.

(56) References Cited

U.S. PATENT DOCUMENTS 5,160,507 A * 11/1992 Horodysky ..................... 44/390

OTHER PUBLICATIONS

Zaramella et al., "A Method of Solid-Phase Synthesis of Oligonucleotide 5'-Peptide-Conjugates Using Acid-Labile [alpha]-Amino Protections," J. Amer. Chem. Soc., 126(43), 14029-14035 (Oct. 6, 2004).*
Spencer J. Williams et al., "Synthesis and Testing of Mechanism-Based Protein-Profiling Probes for Retaining Endo-glycosidases", ChemBioChem 2006, 7, pp. 116-124.

* cited by examiner

*Primary Examiner* — Lawrence E Crane
(74) *Attorney, Agent, or Firm* — Lexyoume IP Group, PLLC

(57) ABSTRACT

A method for preparing amino linker oligonucleotides is provided. More specifically, a method of preparing 5'-amino-linker oligonucleotides comprising the steps of: introducing an amino linker having a protecting group into the 5' terminus of an oligonucleotide; and removing the protecting group from the amino linker oligonucleotide by contacting with acetic acid and 2,2,2-trifluoroethanol is provided. The amino protecting group is efficiently removed from the amino linker oligonucleotides, and thereby achieving a high yield of the amino linker oligonucleotides.

16 Claims, 2 Drawing Sheets

SEQUENCE LISTING

```
<160> NUMBER OF SEQ ID NOS: 4

<210> SEQ ID NO 1
<211> LENGTH: 15
<212> TYPE: DNA
<213> ORGANISM: Artificial Sequence
<220> FEATURE:
<223> OTHER INFORMATION: oligonucleotide 1

<400> SEQUENCE: 1
ggttggtgtg gttgg                                                  15

<210> SEQ ID NO 2
<211> LENGTH: 34
<212> TYPE: DNA
<213> ORGANISM: Artificial Sequence
<220> FEATURE:
<223> OTHER INFORMATION: oligonucleotide 2

<400> SEQUENCE: 2
cccagaggga agactttagg ttcggttcac gtcc                             34

<210> SEQ ID NO 3
<211> LENGTH: 28
<212> TYPE: DNA
<213> ORGANISM: Artificial Sequence
<220> FEATURE:
<223> OTHER INFORMATION: oligonucleotide 3

<400> SEQUENCE: 3
ttggtggtgg tggttgtggt ggtggtgg                                    28

<210> SEQ ID NO 4
<211> LENGTH: 10
<212> TYPE: DNA
<213> ORGANISM: Artificial Sequence
```

```
<220> FEATURE:
<223> OTHER INFORMATION: oligonucleotide 4

<400> SEQUENCE: 4
tttttttttt                                                            10
```

METHOD OF PREPARING 5'-AMINO-LINKER OLIGONUCLEOTIDES DERIVATIVES AND ANALOGOUS 5'-LABELED-LINKER OLIGONUCLEOTIDES THEREFROM

CROSS-REFERENCE TO RELATED APPLICATIONS

This application claims priority to and the benefit of U.S. Provisional Application No. 61/097,365 filed in the United States Patent and Trademark Office on Sep. 16, 2008, the entire contents of which are incorporated herein by reference.

BACKGROUND OF THE INVENTION

Provided is a method of preparing amino linker oligonucleotides with a high yield by efficiently removing an amino protecting group from amino linker oligonucleotides protected with the protecting group, and a method of preparing labeled linker oligonucleotides with a high yield from the amino linker oligonucleotides.

In the preparation of labeled oligonucleotides, the following two methods have generally been used to introduce a label such as biotin, fluorescein, thiol, cholesterol, and the like, to 5' terminus of oligonucleotides; a solid phase labeling technique (phosphoramidite coupling) using an expensive labeling phosphoramidite agents, and a liquid phase labeling technique using labeling agents in the form of N-hydroxy succinimide ester.

Examples of the agents used for the phosphoramidite coupling include fluorescein phosphoramidite, cholesteryl phosphoramidite, 5'-biotin phosphoramidite, thiol-modifier C6 SS, and the like. There is a problem that the agents used for the phosphoramidite coupling are too expensive. Another problem is that the agents once resolved in liquid are so unstable that reaction yields decrease quickly, as the storage time is longer. FIG. 1 briefly illustrates a labeling method using the phosphoramidite coupling, wherein the prices of the labeling agents used are also recited.

Meanwhile, the liquid phase labeling method using agents in the form of N-hydroxy succinimide ester has difficulties in separation and filtration, and thus, there are some limits in using the liquid phase labeling for the preparation of labeled oligonucleotides.

Besides, there are other methods using amino linkers to prepare labeled oligonucleotides. The method for preparing labeled oligonucleotides using amino linkers generally has a problem of low yields compared to when the solid phase phosphoramidite coupling is employed. That is because amino protecting groups are not completely removed from oligonucleotides, unlike peptides, such that the yield of deprotected amino linker oligonucleotides is lowered. A yield for the removal of amino protecting groups is reported to be approximately 50% in the method for preparing labeled oligonucleotides using amino linkers (Zaramella, S., et al, J. Am. Chem. Soc., 2004, 126, 14029-14035).

In this context, there is a growing interest in developing an economic method for amino linker oligonucleotides synthesis by quantitatively removing amino protecting groups and achieving a higher yield than that in the phosphoramidite coupling.

SUMMARY OF THE INVENTION

An embodiment provides a method of preparing amino linker oligonucleotides with a high yield by removing an amino protecting group from the amino linker oligonucleotides protected by the protecting group.

Another embodiment provides a method of preparing labeled amino linker oligonucleotides further including the step of introducing a labeling agent into amino linker oligonucleotides.

DETAILED DESCRIPTION OF THE EMBODIMENTS

An embodiment relates to a method of preparing amino linker oligonucleotides comprising the following steps of:
introducing an amino linker with a protecting group into the 5' terminus of an oligonucleotide; and
removing the protecting group from the amino linker oligonucleotide protected with the protecting group in the presence of acetic acid and 2,2,2-trifluoroethanol ($F_3CCH_2OH$).

Another embodiment relates to a method of preparing labeled amino linker oligonucleotides further including the step of binding a labeling agent to the amino group of the amino linker oligonucleotides.

Figure 2:
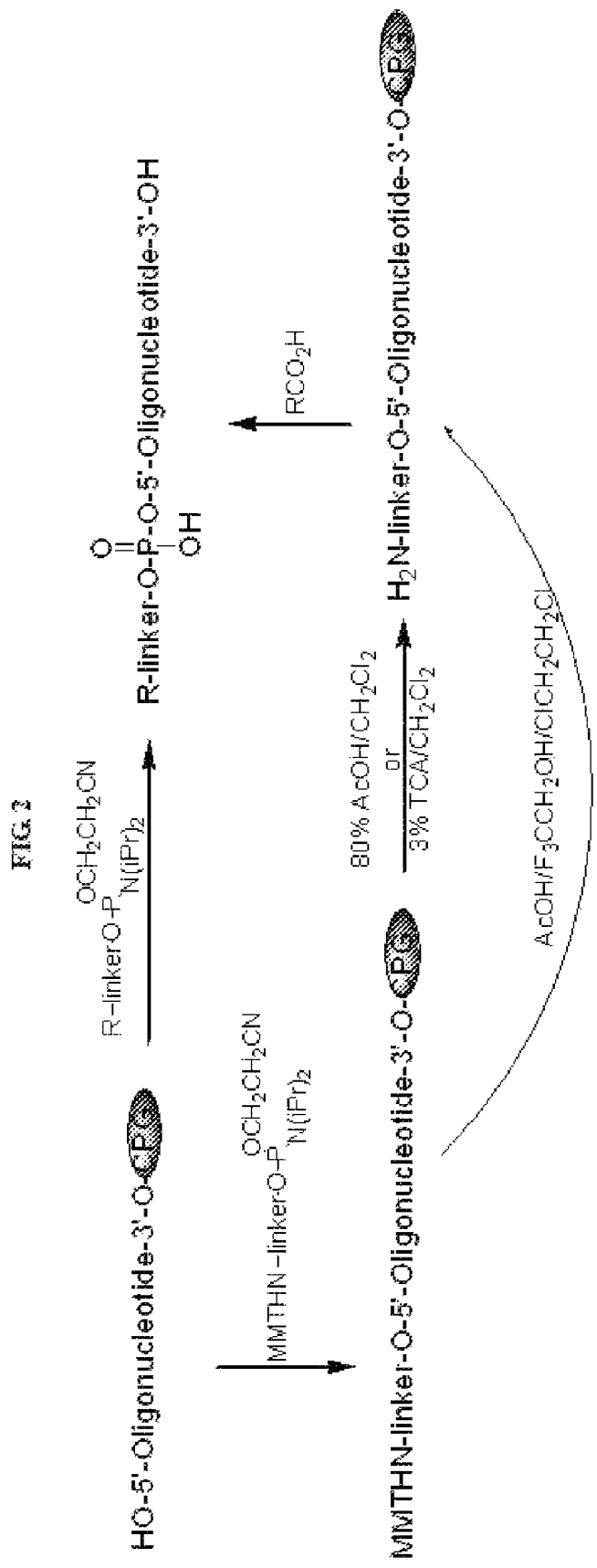
FIG. 2 shows yields for the phosphoramidite coupling and the labeling methods using amino linker oligonucleotides according to the present invention.

FIG. 2 shows a comparison between the chemical reaction processes of labeled oligonucleotides synthesis by the methods using the phosphoramidite coupling and using amino linker oligonucleotides. Final yields for labeled oligonucleotides using the phosphoramidite coupling were 70~80%. The preparation method of amino linker oligonucleotides includes the steps of introducing an amino linker with a protecting group into the 5' terminus of an oligonucleotide, removing the protecting group, and binding a labeling agent to the amino group. However, the removal of the amino protecting group in the sole presence of acetic acid or trichloroacetic acid (TAC) falls short of completely removing the amino protecting group, or causes the problem of low yields due to side reactions such as acetylation of the amino group.

In contrast, a yield for amino linker oligonucleotides according to an embodiment of the present invention is 90% at the step of removing the amino protecting groups from the amino linker oligonucleotides protected by the protecting group. The removal of the amino protecting groups from the amino linker oligonucleotides protected by the protecting groups are performed in the presence of acetic acid or 2,2,2-trifluoroethanol.

Figure 1:
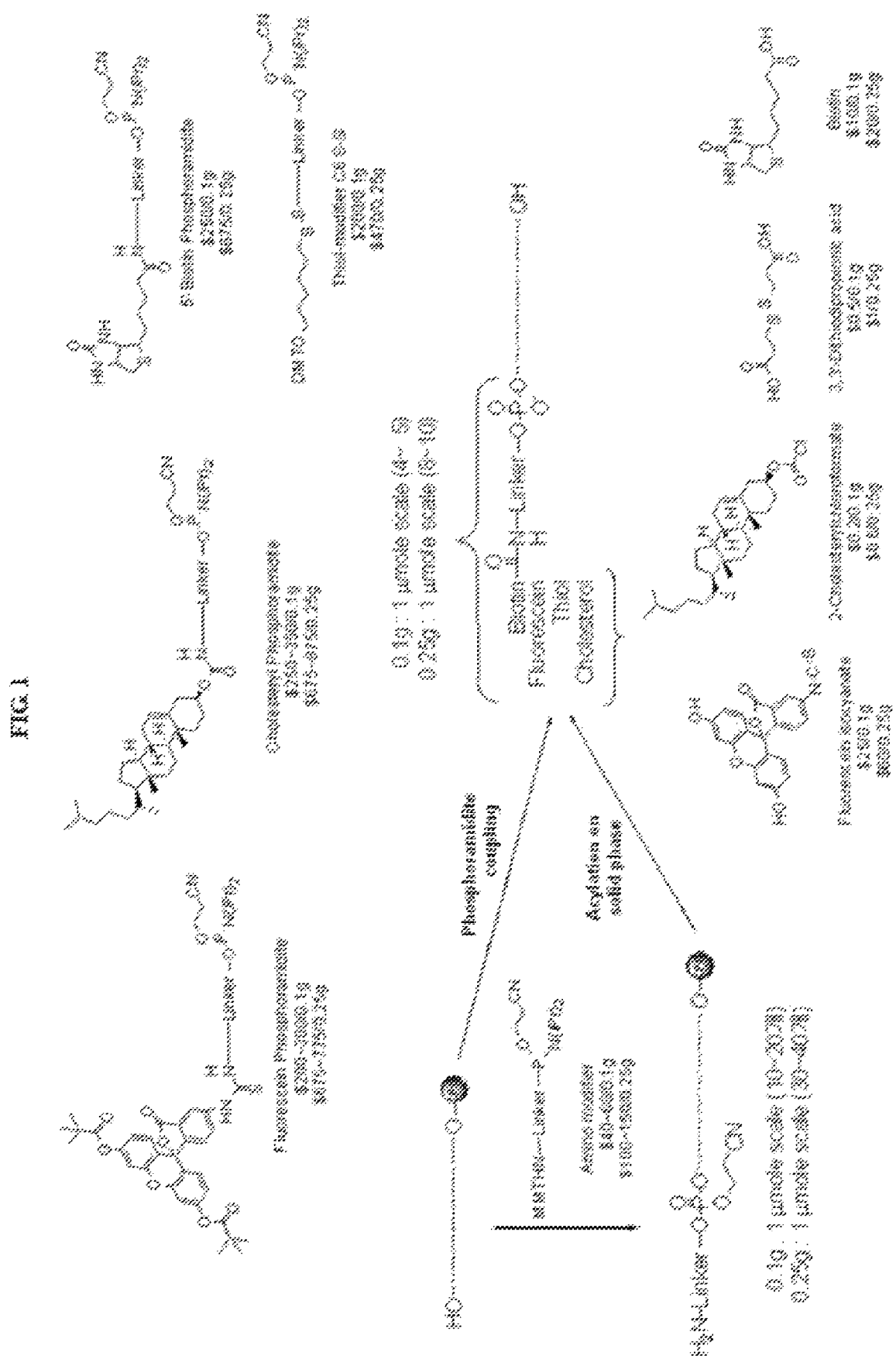
FIG. 1 shows a comparison in chemical reaction processes between the phosphoramidite coupling and the labeling agent binding process using amino linker oligonucleotides according to the present invention, and the prices of agents used for respective processes.

FIG. 1 discloses the prices of labeling agents used in the chemical reaction processes, for the method using the phosphoramidite coupling and for the method for labeled oligonucleotides synthesis by the amino linker oligonucleotides preparation according to the present invention. The prices of labeling agents used for the method using amino linker oligonucleotides are ⅛ lower, at least, or 1/1,750 lower than those of labeling agents used for the phosphoramidite coupling.

Hereinafter, The method according to embodiments of the present invention will be described in detail.

In one embodiment, a preparation method of amino linker oligonucleotides includes the steps of introducing an amino linker with a protecting group into the 5' terminus of an oligonucleotide; and removing the protecting group from the amino linker oligonucleotides protected by the protecting groups are performed in the presence of acetic acid or 2,2,2-trifluoroethanol.

The oligonucleotide may be one prepared by a solid-phase reaction, wherein there is no special limitation on the types and conditions of the solid phase reaction to be used. Since oligonucleotides are generally synthesized in continuous sequences, it is preferred to prepare oligonucleotides by solid phase oligonucleotide synthesis than by reactions in liquid in order to achieve high level of purity. Therefore, the preparation method may further include the step of preparing an oligonucleotide through a solid-phase reaction prior to the step of introducing an amino linker with a protecting group into the 5' terminus of the oligonucleotide.

In the step of introducing an amino linker having a protecting group into 5' terminus of the oligonucleotide, the protecting group in the amino linker may be an amino protecting group generally known in organic synthesis. Preferably, the amino protecting group may be selected from the group consisting of monomethoxytrityl (MMT), 6-(4,4'-Dimethoxy-4''-methylsulfonyl-tritylamino (DMS(O)MT), 2-(Biophenyl-4-yl)propan-2-yloxycarbonyl (Bpoc), and 2-(3,5-dimethoxyphenyl)propan-2-yloxycarbonyl (Ddz). It is preferred to introduce an amino linker protected by a monomethoxytrityl (MMT) group into the 5' terminus of the oligonucleotide.

A linker may be used, wherein the linker may be a carbon chain having 1 to 30 carbons or polyethylene glycol presented by $(CH_2CH_2O)n$ (n=2 to 400)

In another embodiment, the introduction of the amino linker having the protecting group into the 5' terminus of the oligonucleotide may be performed on the oligonucleotide which is bound to a bead. Preferably, the bead may be Controlled Pore Glass bead (CPG bead).

The step of removing the protecting group from the protected amino linker oligonucleotides may be performed in the presence of acetic acid and trifluoroethanol (e.g., 2,2,2-trifluoroethanol). Acetic acid and 2,2,2-trifluoroethanol may be used as a form dissolved in organic solvent. Preferably, the ratio of acetic acid:2,2,2-trifluoroethanol ($F_3CCH_2OH$):organic solvent may be 1:1~5:5~10 by volume.

To achieve a high removal rate for amino protecting groups, the ratio of acetic acid:2,2,2-trifluoroethanol ($F_3CCH_2OH$):organic solvent may preferably be 1:1~5:5~10 by volume. More preferably, the ratio of acetic acid:2,2,2-trifluoroethanol($F_3CCH_2OH$):organic solvent may be 1:1~3:5~8 by volume.

Most preferably, the ratio of acetic acid:2,2,2-trifluoroethanol($F_3CCH_2OH$):organic solvent may be 1:2:7 by volume.

The organic solvent may be one widely and conventionally in laboratories, and any one capable of dissolving acetic acid and 2,2,2-trifluoroethanol therein can be used as the organic solvent. For example, the organic solvent may be one or more selected from the group consisting of dichloromethane, dichloroethane, dimethyl formamide (DMF), acetonitrile (AcCN), dimethyl sulfoxide (DMSO), alcohol having 1 to 4 carbons (e.g. ethanol (EtOH), methanol (MeOH)), and N-Methylpyrrolidinone (NMP), but not be limited thereto. Preferably, dichloromethane ($CH_2Cl_2$)), dichloroethane ($ClCH_2CH_2Cl$), or a combination thereof may be used.

In the present invention, the protecting group is removed from the amino group by the use of acetic acid and trifluoroethanol, to significantly increase the efficiency in protecting group removal, allowing the labeling efficiency of amino group to be improved, wherein the high efficiency of labeling can be achieved by the use of only a conventional agent, without using an expensive ones.

In one embodiment, a step of binding a labeling agent to the amino group on the amino linker oligonucleotides may be further included. The labeling agent used may be one or more selected from the group consisting of carboxylic acids, dehydrates having thiol group, chloroformates, thiol anhydrides, isocyanates, and chelates.

The carboxyl acids used as a labeling agent may be selected from the group consisting of including biotin, Biotin-Lys (Biotin), and Biotin-Cys (Biotin).

The anhydrides having thiol group used as a labeling agent may be of any one without any limitation so long as it allows acylation reaction with the amino group. For example, 3,3'-dithiopropionic anhydride may be used.

The chloroformates used as a labeling agent may be selected from the group consisting of fluorescein chloroformates, thiol chloroformates, cholesterol chloroformates, and the like, but not be limited thereto. For example, a cholesteryl chloroformate may be used.

The isocyanates used as a labeling agent may be any isocyanates conventionally used as labeling agents with no limitation, and, for example, one or more selected from the group consisting of fluorescein isocyanates, thiol isocyanates, and cholesterol isocyanates. Preferably, fluorescein 5(6)-isocyanate may be used.

The chelates used as a labeling agent may be of any one without any limitation so long as it has a functional group capable of forming a binding to an amino group. For example, it may be selected from the group consisting of 1,4,7,10-Tetraazacyclododecane-1,4,7-tris-tert-butyl acetate-10-acetic acid, 1,4,7,10-tetrazadodecane-N,N',N'',N'''-tetraacetic acid (DTPA), Diethylenetriamine-N,N,N'',N'''-tetra-tert-butyl acetate-N'-acetic acid, DTPA-tetra(t-Bu ester)], 1,4,7,10-Tetraazacyclododecane-1,4,7-tris-tert-butyl acetate-10-(N-a-Fmoc-N-e-acetamido-L-lysine), Fmoc-L-Lys-mono-amide-DOTA-tris(t-Bu ester), and the like. Preferably, DTPA-tetra (t-Bu ester) may be used.

In a concrete embodiment, the labeled oligonucleotide may be labeled with one selected from the group consisting biotin, fluorescein, thiol, Macrocyclic DOTA, and cholesterol.

As described above, the preparation method for amino linker oligonucleotides according to the present invention can achieve a removal of the amino protecting group with higher efficiency, and thereby improving the synthesis efficiency of amino linker oligonucleotides.

In addition, the present invention may provide a method of binding conventionally used labeling agents to the amino group of amino linker oligonucleotides, to provide a preparation method of labeled oligonucleotides having advantages in aspect of cost and yield, thereby solving the problem of the existing high-priced methods.

Therefore, the preparation method of amino linker oligonucleotides and the accordingly enabled preparation method of labeled linker oligonucleotides, according to the present invention, can be used in mass-production of labeled linker oligonucleotides in industry scale in an efficient and economic manner.

EXAMPLES

The present invention is further explained in more detail with reference to the following examples. These examples, however, should not be interpreted as limiting the scope of the present invention in any manner. Below is the detailed explanation of the present invention by the examples of the present inventions and comparative examples.

The amino linker oligonucleotides used in the examples and the comparative examples were prepared as follows: After an oligonucleotide was prepared by a solid-phase reaction using Mermade DNA/RNA synthesizer (Bioautomation), an amino linker having a protecting group was introduced at the 5' terminus of the oligonucleotide. The introduction of the amino linker having the protecting group, as used in the examples and the comparative examples, was performed on the oligonucleotide bound to the Controlled Pore Glass (CPG) bead. In the examples and the comparative examples, a monomethoxytrityl group was used as the protecting group of the amino linker.

Presented below are the examples according to the present invention and the comparative examples to show a comparison with the examples according to the present invention.

Example 1

Removal of the Protecting Group from Amino Linker Oligonucleotides in the Presence of Acetic Acid and Trifluoroethanol Using Mermade 12 solid phase synthesizer (bioautomation Inc., U.S.A.) and an oligonucleotide synthesis protocol as commercially provided, amino linker oligonucleotides bound to CPG were prepared as MMT-HN-Linker-oligonucleotide-CPG. The prepared amino linker oligonucleotide were put into a 1 mL of a mixture in which acetic acid, 2,2,2-trifluoroethanol, and dichloroethane (in the concentrations of 10%, 20%, and 70% by volume, respectively) are mixed with the ratio of 1:2:7 by volume and stirred for 30 minutes. The bead was washed with dimethylformamide and dichloromethane, each three times. Then, 2 mL of saturated $NH_4OH$ was added thereto, and the mixture was placed at 60° C. for 8 hours.

The solid part was isolated out from the centrifuge. The liquid part was collected and dried under vacuum. The obtained amino linker oligonucleotides were purified by RP-HPLC and freeze-dried, to obtain the pure entitled compound in solid phase. In this example, the yield for amino linker oligonucleotides, from which the protecting groups are removed, was 90%.

$H_2N(CH_2)_6$—O-5'-GGTTGGTGTGGTTGG-3'-OH [$H_2N(CH_2)_6$—O-(SEQ ID NO: 1)-OH]
Mass/ESI: 4904.32 (Cal., 4905.20)

$H_2N(CH_2)_6$—O-5'-CCCAGAGGGAAGACTTTAGGTTCGGTTCACGTCC-3'-OH [$H_2N(CH_2)_6$—O-(SEQ ID NO: 2)-OH]
Mass/ESI: 10635.85 (Cal., 10637.96)
179.16

$H_2N(CH_2)_6$—O-O-5'-TTGGTGGTGGTGGTTGTGGTGGTGGTGG-3'-OH [$H_2N(CH_2)_6$—O-(SEQ ID NO: 3)-OH]
Mass/ESI: 9058.87 (Cal., 9059.96)

$H_2N(CH_2)_6$—O-5'-TTTTTTTTTT-'-OH [$H_2N(CH_2)_6$—O-(SEQ ID NO: 4)-OH]
Mass/ESI: 3154.20 (Cal., 3159.16)

Comparative Example 1

Removal of Protecting Groups from Amino Linker Oligonucleotides in the Presence of 80% Acetic Acid An experiment to remove protecting groups from the amino linker oligonucleotides was performed, where all conditions were identical to Example 1 except that a 1 mL of 80% by volume acetic acid/dichloroethane mixture was used, instead of 1 mL of the mixture of acetic acid, 2,2,2-trifluoroethanol, and dichloroethane (in the concentrations of 10%, 20%, and 70% by volume, respectively) with the ratio of 1:2:7 by volume. In this comparative example, the yield for amino linker oligonucleotides from which the protecting groups are removed, was 30%.

$H_2N(CH_2)_6$—O-5'-GGTTGGTGTGGTTGG-3'-OH [$H_2N(CH_2)_6$—O-(SEQ ID NO: 1)-OH])
Mass/ESI: 4904.21 (Cal., 4905.20),

Comparative Example 2

Removal of Protecting Groups from Amino Linker Oligonucleotides in the Presence of 3% Trichloroacetic Acid (TCA)

An experiment to remove amino protecting group from the amino linker oligonucleotides was performed as in Comparative Experiment 1, with all conditions identical thereto, except that 1 mL of 3% trichloroacetic acid/acetonitrile mixture was used, instead of 1 mL of 80% acetic acid/dichloroethane mixture. In Comparative Example 2, the yield for amino linker oligonucleotides, from which the protecting groups are removed, was 50%.

$H_2N(CH_2)_6$—O-5'-GGTTGGTGTGGTTGG-3'-OH [$H_2N(CH_2)_6$—O-(SEQ ID NO: 1)-OH]
Mass/ESI: 4904.12 (Cal., 4905.20), The above results show that the yield of 90% for amino linker oligonucleotides from which the protecting groups are removed can be achieved in the presence of both of acetic acid and trifluoroethanol, where the yield of 90% is significantly higher than 30~50% which are the yields for amino linker oligonucleotides from which the protecting groups are removed in the presence of only one, acetic acid or trichloroacetic acid (TCA). In addition, the yield of 90% is also higher than 80%, which is the yield for amino linker oligonucleotides through the phosphoramidite coupling. Therefore it is found that labeled oligonucleotides can be prepared with a high yield and in an economic manner.

Example 2

Binding of Labeling Agents to the Amino Group of the Amino Linker Oligonucleotides Hereinafter, representative examples in which various labeling agents are bound to an amino group of amino linker oligonucleotides are provided.

2.1: Labeling the Amino Linker Oligonucleotides Prepared in Example 1 with Biotin (Biotinylation)

Biotin 0.05 g (20 µmole), benzotriazol-1-yl-oxytripyrrolidinophosphonium hexafluorophosphate (PyBOP) 0.10 g (20 µmole), hydroxybenzotriazole (HOBt) 0.03 g (20 µmole) and N-methylmorpholine (NMM) 0.04 mL (40 µmole) were dissolved in 1 mL dimethylformamide (DMF) and stirred for 1 minute. Then, the mixture was contacted with beads to which the amino linker oligonucleotides (1 µmole) prepared in Example 1 were bound, and stirred for 1 hour. The beads were washed with dimethylformamide and dichloromethane, each three times, added with 2 mL saturated $NH_4OH$, and placed at 60° C. for 8 hours. The solid part was isolated out from the centrifuge, and the liquid part was collected and dried under vacuum. The obtained biotin-labeled oligonucleotides were purified by RP-HPLC and freeze-dried, to produce the pure entitle compound in solid phase.

```
Biotinyl-HN(CH₂)₆-O-5'-CCCAGAGGGAAGACTTTAGGTTCGGTT
CACGTCC-3'-OH [Biotinyl-HN(CH₂)₆-O-(SEQ ID NO: 2)-
OH],
Mass/ESI: 10,866.90 (Cal. 10,864.18)
```

2.2: Labeling the Amino Linker Oligonucleotides Prepared in Example 1 with Fluorescein (Fluorescein Coupling)

0.03 g of Fluorescein 5(6)-isocyanate (20 μmole) was dissolved in 1 mL dimethylformamide (DMF). Then the mixture was contacted with beads to which the amino linker oligonucleotides (1 μmole) prepared in Example 1 were bound, and stirred for 1 hour. The beads were washed with dimethylformamide and dichloromethane, each three times. To the beads, 2 mL saturated NH₄OH was added and the mixture was placed at 60° C. for 8 hours. The solid part was isolated out from the centrifuge, and the liquid part was collected and dried under vacuum. The obtained fluorescein-labeled oligonucleotides were purified by RP-HPLC and freeze-dried, to produce the pure entitle compound in solid phase.

```
FITC-HN(CH₂)₆-O-5'-GGTTGGTGTGGTTGG-3'-OH [FITC-
HN(CH₂)₆-O-(SEQ ID NO: 1)-OH]
Mass/ESI: 5293.22 (Cal., 5294.59),
```

2.3: Labeling the Amino Linker Oligonucleotides Prepared in Example 1 with Thiol (Thiolation).

0.04 g of dithiopropionic anhydride (20 μmole) was dissolved in 1 mL dimethylformamide (DMF). Then the mixture was contacted with beads to which the amino linker oligonucleotides (1 μmole) prepared in Example 1 were bound, and stirred for 1 hour. The beads were washed with dimethylformamide and dichloromethane, each three times. Subsequently it was added with 2 mL saturated NH₄OH and placed at 60° C. for 8 hours. The solid part was isolated out from the centrifuge, and the liquid part was collected and dried under vacuum. The obtained 3,3'-dithiopropionyl-labeled oligonucleotides were purified by RPHPLC and freeze-dried, to produce the pure entitle compound in solid phase.

```
HO₂C(CH₂)₂SS(CH₂)COHN(CH₂)₆-O-5'-GGTTGGTGTGGTTGG-
3'-OH [HO₂C(CH₂)₂SS(CH₂)₂COHN(CH₂)₆-O-(SEQ ID
NO: 1)-OH]
Mass/Maldi: 5098.92 (cal. 5097.46)
```

2.4: Labeling the Amino Linker Oligonucleotides Prepared in Example 1 with Cholesterol (Cholesterylation)

0.04 g of cholesteryl chloroformate (20 μmole) and 0.15 mL of N,N Diisopropylethylamine (DIPEA) were dissolved in 1 mL dimethylformamide (DMF). Then the mixture was contacted with beads to which the amino linker oligonucleotides (1 μmole) prepared in Example 1 were bound, and stirred for 1 hour. The beads were washed with dimethylformamide and dichloromethane, each three times. Subsequently, to the beads, 2 mL saturated NH₄OH was added, and the mixture was placed at 60° C. for 8 hours. The solid part was isolated out from the centrifuge, and the liquid part was collected and dried under vacuum. The obtained cholesterol-labeled oligonucleotides were purified by RP-HPLC and freeze-dried, to produce the pure entitle compound in solid phase.

```
Cholesterol-HN(CH₂)₆-O-5'-GGTTGGTGTGGTTGG-3'-OH
[Cholesterol-HN(CH₂)₆-O-(SEQ ID NO: 1)-OH]
Mass/ESI: 5316.88 (cal. 5317.85)
```

2.5: Labeling the Amino Linker Oligonucleotides Prepared in Example 1 with a Chelate (Chelator Labeling)

0.06 g of 1,4,7,10-Tetraazacyclododecane-1,4,7-tris-tert-butyl acetate-10-acetic acid (DOTA-tris(t-Bu ester) (20 μmole), 0.10 g of benzotriazol-1-yloxytripyrrolidinophosphonium hexafluorophosphate (PyBOP) (20 μmole), 0.03 g of Hydroxybenzotriazole (HOBt) (20 μmole) and 0.04 mL of N-methylmorpholine (NMM) (40 μmole) were dissolved in 1 mL dimethylformamide (DMF) and stirred for 1 minute. Then the mixture was contacted with beads to which the amino linker oligonucleotides (1 μmole) prepared in Example 1 were bound, and stirred for 1 hour. The beads were washed with dimethylformamide and dichloromethane, each three times. Subsequently, to the beads, 1 mL of a mixture of TFA (trifluoroacetic acid), TIS (triisopropylsilane) and water ($H_2O$) (in the mixture ratio of 95:2.5:2.5 by volume) was added, and stirred for three hours. The beads were washed with dimethylformamide and dichloromethane, each three times. Subsequently, to the beads, 2 mL of saturated NH₄OH was added and placed at 60° C. for 8 hours. The solid part was isolated out from the centrifuge, and the liquid part was collected and dried under vacuum. The obtained DOTA-labeled oligonucleotides were purified by RP-HPLC and freeze-dried, to produce the pure entitle compound in solid phase.

```
DOTA-HN(CH₂)₆-O-5'-TTGGTGGTGGTGGTTGTGGTGGTGGTGG-
3'-OH [DOTA-HN(CH₂)₆-O-(SEQ ID NO: 3)-OH],
Mass/ESI: 9487.82 (cal. 9489.18)
```

2.6: Labeling the Amino Linker Oligonucleotides Prepared in Example 1 with Fluorescein (Fluorescein Coupling)

Boc-Cys (NPys)-OH; Nα-(t-Butoxycarbonylamino)-S-(3-nitro-2-pyridyl)-L-cysteine (0.08 g, 20 μmole), benzotriazol-1-yl-oxytripyrrolidinophosphonium hexafluorophosphate (PyBOP) (0.10 g, 20 μmole), Hydroxybenzotriazole (HOBt) (0.03 g, 20 μmole) and N-methylmorpholine (NMM) (0.04 mL, 40 μmole) were dissolved in 1 mL dimethylformamide (DMF) and stirred for 1 minute. Then the mixture was contacted with beads to which the amino linker oligonucleotides (1 μmole) prepared in Example 1 were bound, and stirred for 1 hour. After being washed with dimethylformamide and dichloromethane, each three times, the beads were placed in 25% TFA/$CH_2Cl_2$ and stirred for 30 minutes. The beads were washed with dimethylformamide and dichloromethane, each three times. Fluorescein 5(6)-isocyanate (0.03 g, 20 μmole) was dissolved in 1 mL dimethylformamide (DMF), and then, contacted with beads to which the amino linker oligonucleotides (1 μmole) were bound. The beads were stirred for 1 hour. After the beads were washed with dimethylformamide and dichloromethane, each three times, to the beads 2 mL of saturated NH₄OH was added and placed at 60° C. for 8 hours. The solid part was isolated out from the centrifuge, and the liquid part was collected and dried under vacuum. The obtained fluorescein-labeled oligonucleotides were purified by RP-HPLC and freeze-dried, to generate the pure entitle compound in solid phase.

```
Thrombin aptamer
FITC-Cys(NPys)-HN(CH₂)₆-O-5'-GGTTGGTGTGGTTGG-3'-OH
[FITC-Cys(NPys)-HN(CH₂)₆-O-(SEQ ID NO: 1)-OH]
Mass/ESI: 5505.01 (Cal. 5506.88),
```

2.7: Labeling the Amino Linker Oligonucleotides Prepared in Example 1 with Biotin Boc-Lys (Boc)-OH; Di-(t-Butoxycarbonylamino)-L-lysine (0.11 g, 20 µmole), benzotriazol-1-yl-oxytripyrrolidinophosphonium hexafluorophosphate (PyBOP) (0.10 g, 20 µmole), Hydroxybenzotriazole (HOBt) (0.03 g, 20 µmole) and N-methylmorpholine (NMM) (0.04 mL, 40 µmole) were dissolved in 1 mL dimethylformamide (DMF) and stirred for 1 minute. Then the mixture was contacted with beads to which the amino linker oligonucleotides (1 µmole) prepared in Example 1 were bound, and stirred for 1 hour. After being washed with dimethylformamide and dichloromethane, each three times, the bead was placed in 25% TFA/CH$_2$Cl$_2$ and stirred for 30 minutes. The bead was washed with dimethylformamide and dichloromethane, each three times. Biotin (0.05 g, 20 µmole), benzotriazol-1-yl-oxytripyrrolidinophosphonium hexafluorophosphate (PyBOP) (0.10 g, 20 µmole), Hydroxybenzotriazole (HOBt) (0.03 g, 20 µmole) and NMM (0.04 mL, 40 µmole) were dissolved in 1 mL dimethylformamide (DMF) and were stirred for 1 minute. Then, the mixture was contacted with beads to which the amino linker oligonucleotides (1 µmole) were bound. The beads were stirred for 1 hour, and washed with dimethylformamide and dichloromethane, each three times. To the beads, 2 mL of saturated NH$_4$OH was added and placed at 60° C. for 8 hours. The solid part was isolated out from the centrifuge, and the liquid part was collected and dried under vacuum. The obtained biotin-labeled oligonucleotides were purified by RP-HPLC and freeze-dried, to produce the pure entitle compound in solid phase.

Biotin-Lys(Biotin)-HN(CH$_2$)$_6$-O-5'-TTTTTTTTT-3'-OH
[Biotin-Lys(Biotin)-HN(CH$_2$)$_6$-O-(SEQ ID NO: 4)-OH],
Mass/ESI: 3737.83 (Cal. 3739.89), From the above embodiments and the results of the examples, it can be found that removal rates of the protecting groups from the amino linker oligonucleotides are high where the removal of the protecting groups is performed in the both presence of acetic acid and 2,2,2-trifluoroethanol. In addition, it has been confirmed that labeled oligonucleotides can be produced by binding various labeling agents to amino linker oligonucleotides as prepared following the methods above. Thus the present invention enables oligonucleotides synthesis at low cost and bindings of various labeling agents simultaneously, such that production of labeled oligonucleotides can be achieved in a more convenient and economic manner.

---

What is claimed is:

1. A method of preparing 5'-amino linker oligonucleotides, comprising the steps of:
   introducing an amino linker having a protecting group at the 5' terminus of an oligonucleotide; and
   removing the protecting group from the amino linker oligonucleotide by contacting with a mixture of acetic acid and trifluoroethanol ($F_3CCH_2OH$)
   wherein the linker is a carbon chain having 1 to 30 carbons or polyethylene glycol presented by $(CH_2CH_2O)n$ (n=2 to 400), and
   the protecting group is selected from the group consisting of monomethoxytrityl (MMT), 6-(4,4'-Dimethoxy-4"-methylsulfonyl-trityl) (DMS(O)MT), 2-(Biophenyl-4-yl)propan-2-yloxycarbonyl (Bpoc), and 2-(3,5-dimethoxyphenyl)propan-2-yloxycarbonyl (Ddz) groups.

2. The method according to claim 1, wherein the mixture of acetic acid and trifluoroethanol ($F_3CCH_2OH$) is prepared by dissolving acetic acid and trifluoroethanol in an organic solvent with the volume ratio of acetic acid:trifluoroethanol: organic solvent being 1:1~5:5~10.

3. The method according to claim 2, wherein the organic solvent is one or more selected from the group consisting of dichloromethane, dichloroethane, dimethyl formamide (DMF), acetonitrile (AcCN), dimethyl sulfoxide (DMSO), alcohol having 1 to 4 carbons, and N-methylpyrrolidinone (NMP).

4. The method according to claim 1, wherein the protecting group is monomethoxytrityl (MMT).

5. The method according to claim 1, further comprising the step of preparing said oligonucleotide by solid phase reaction prior to the step of introducing an amino linker with a protecting group into the 5' terminus of an oligonucleotide.

6. A method of preparing 5'-labeled linker oligonucleotides comprising the steps of:
   introducing an amino linker having a protecting group at the 5' terminus of an oligonucleotide;
   removing the protecting group from the amino linker oligonucleotide by contacting with a mixture of acetic acid and trifluoroethanol ($F_3CCH_2OH$); and
   binding a labeling agent to the amino group of the amino linker oligonucleotides
   wherein the linker is a carbon chain having 1 to 30 carbons or polyethylene glycol presented by $(CH_2CH_2O)n$ (n=2 to 400), and
   the protecting group is selected from the group consisting of monomethoxytrityl (MMT), 6-(4,4'-Dimethoxy-4"-methylsulfonyl-trityl) (DMS (O)MT), 2-(Biophenyl-4-yl)propan-2-yloxycarbonyl (Bpoc), and 2-(3,5-dimethoxyphenyl)propan-2-yloxycarbonyl(Ddz) groups.

7. The method according to claim 6, wherein the mixture of acetic acid and trifluoroethanol ($F_3CCH_2OH$) is prepared by dissolving acetic acid and trifluoroethanol in an organic solvent with the volume ratio of acetic acid:trifluoroethanol (F3CCH2OH):organic solvent being 1:1~5:5~10.

8. The method according to claim 7, wherein the organic solvent is one or more kinds selected from the group consisting of dichloromethane, dichloroethane, dimethyl formamide (DMF), acetonitrile (AcCN), dimethyl sulfoxide (DMSO), alcohol of carbon number 1 to 4, and N-methylpyrrolidinone (NMP).

9. The method according to claim 6, wherein the protecting group is selected from the group consisting of monomethoxytrityl (MMT).

10. The method according to claim 6, further comprising the step of preparing the oligonucleotide by solid phase reaction prior to the step of introducing an amino linker with a protecting group into the 5' terminus of an oligonucleotide.

11. The method according to claim 6, wherein the labeling agent is one or more selected from the group consisting of a carboxylic acid, a chloroformate, a thiol anhydride, an isocyanate, and a chelate having a functional group capable of binding to an amino group.

12. The method according to claim 11, wherein the carboxylic acid is selected from the group consisting of biotin, Biotin-Lys (Biotin), and Biotin-Cys (Biotin).

13. The method according to claim 11, wherein the anhydride having thiol group is 3,3-dithiopropionic anhydride.

14. The method according to claim 11, wherein the chloroformate is selected from the group consisting of a fluorescein chloroformate, a thiol chloroformate, and a cholesterol chloroformate.

15. The method according to claim 11, wherein the isocyanate is selected from the group consisting of fluorescein isocyanates, thiol isocyanates, and cholesterol isocyanates.

16. The method according to claim 11, wherein the chelate is selected from the group consisting of 1,4,7,10-Tetraazacyclododecane-1,4,7-tris-tert-butyl acetate-10-acetic acid, 1,4, 7,10-tetrazadodecane-N,N',N'',N'''-tetraacetic acid (DTPA), Diethylenetriamine-N,N,N'',N''-tetra-tert-butyl acetate-N'-acetic acid, DTPA-tetra(t-Bu ester), 1,4,7,10-Tetraazacyclododecane-1,4,7-tris-tert-butylacetate-10-(N-a-Fmoc-N-e-acetamido-L-lysine), and Fmoc-L-Lys-mono-amide-DOTA-tris(t-Bu ester).

* * * * *